United States Patent
Gagliano et al.

(10) Patent No.: US 9,277,918 B2
(45) Date of Patent: Mar. 8, 2016

(54) KNOTLESS SUTURE SYSTEM

(75) Inventors: Jeffrey Gagliano, Boulder, CO (US); Seth M. Hootstein, New York, NY (US)

(73) Assignee: ArthroCare Corporation, Austin, TX (US)

( * ) Notice: Subject to any disclaimer, the term of this patent is extended or adjusted under 35 U.S.C. 154(b) by 59 days.

(21) Appl. No.: 13/300,833

(22) Filed: Nov. 21, 2011

(65) Prior Publication Data

US 2012/0209325 A1    Aug. 16, 2012

Related U.S. Application Data

(60) Provisional application No. 61/417,081, filed on Nov. 24, 2010.

(51) Int. Cl.
*A61B 17/04* (2006.01)
*A61B 17/06* (2006.01)
*A61F 2/08* (2006.01)

(52) U.S. Cl.
CPC ....... *A61B 17/06166* (2013.01); *A61B 17/0401* (2013.01); *A61B 17/0487* (2013.01); *A61B 2017/0403* (2013.01); *A61B 2017/0477* (2013.01); *A61F 2/0811* (2013.01); *A61F 2002/0858* (2013.01); *A61F 2002/0888* (2013.01)

(58) Field of Classification Search
CPC ............. A61B 17/04; A61B 17/0485; A61B 17/0487; A61B 17/0466; A61B 17/0401; A61B 17/06166; A61B 2017/0461; A61B 2017/0459; A61B 2017/0458; A61B 2017/0414; A61B 2017/0409; A61B 2017/00004; A61B 2017/0403; A61B 2017/0477; A61B 2017/0464; A61B 2017/06019; A61B 2017/06176; A61B 2017/0419; A61B 2017/0496; A61L 17/00; A61L 17/005; A61L 17/04; A61L 17/06; A61L 17/08; A61L 17/10; A61L 17/105; A61L 17/12; A61L 17/14; A61L 17/145
USPC ................. 606/228–233, 139, 144–150, 103; 428/131, 133, 222, 377, 357; 442/204; 87/8, 9, 11, 13; 57/202, 22
See application file for complete search history.

(56) References Cited

U.S. PATENT DOCUMENTS 1,243,337 A * 10/1917 O'Connell .................... 474/253
1,703,269 A *  2/1929 Garris ................................ 87/6
(Continued)

FOREIGN PATENT DOCUMENTS

DE     196 28 909          1/1998    ............. A61B 17/04
FR     2939632 A1 *  6/2010

(Continued)

OTHER PUBLICATIONS

PCT International Search Report for PCT/US01/28190 2pgs, Mailed May 2, 2002.

(Continued)

*Primary Examiner* — David C Eastwood
(74) *Attorney, Agent, or Firm* — Norman F. Hainer, Jr.

(57) ABSTRACT

A knotless suture system formed from two lengths of suture joined at a suture junction point, with at least four suture limbs extending from the suture junction. The knotless suture system provides the ability to construct a suture bridge for soft tissue repair and fixation across a medial and lateral row bone fixation anchor configuration while passing the suture system in a simplified method of suture management.

6 Claims, 8 Drawing Sheets

(56) References Cited

U.S. PATENT DOCUMENTS

| | | | |
|---|---|---|---|
| 2,515,172 A * | 7/1950 | Abbott | 57/22 |
| 2,600,395 A | 6/1952 | Domoj et al. | 87/13 |
| 2,860,393 A * | 11/1958 | Brock | 24/16 PB |
| 3,123,077 A * | 3/1964 | Alcamo | 606/228 |
| 3,634,972 A * | 1/1972 | Illman | 57/202 |
| 3,942,532 A * | 3/1976 | Hunter et al. | 606/231 |
| 4,027,676 A * | 6/1977 | Mattei | 606/230 |
| 4,047,533 A | 9/1977 | Perciaccante et al. | 128/335.5 |
| 4,186,921 A | 2/1980 | Fox | 29/461 |
| 4,319,428 A | 3/1982 | Fox | 47/42 |
| 4,345,339 A | 8/1982 | Muller et al. | 623/13.2 |
| 4,731,084 A | 3/1988 | Dunn et al. | 623/13.19 |
| 4,792,336 A | 12/1988 | Hlavacek et al. | 623/13.18 |
| 4,834,755 A | 5/1989 | Silvestrini et al. | 623/13.19 |
| 4,844,067 A * | 7/1989 | Ikada et al. | 606/231 |
| 4,917,700 A | 4/1990 | Aikins | 623/13.19 |
| 4,946,377 A | 8/1990 | Kovach | 623/13.18 |
| 4,946,467 A | 8/1990 | Ohi et al. | 606/228 |
| 4,962,929 A | 10/1990 | Melton, Jr. | 473/516 |
| 4,987,665 A | 1/1991 | Dumican et al. | 28/218 |
| 5,019,093 A | 5/1991 | Kaplan et al. | 606/228 |
| 5,062,344 A | 11/1991 | Gerker | 87/8 |
| 5,116,373 A * | 5/1992 | Jakob et al. | 623/13.16 |
| 5,217,495 A | 6/1993 | Kaplan et al. | 623/13.18 |
| 5,259,846 A | 11/1993 | Granger et al. | 606/224 |
| 5,263,984 A | 11/1993 | Li | 623/13.18 |
| 5,318,575 A | 6/1994 | Chesterfield et al. | 606/151 |
| 5,376,118 A | 12/1994 | Kaplan et al. | 623/23.72 |
| 5,405,352 A | 4/1995 | Weston | 606/148 |
| 5,450,860 A | 9/1995 | O'Connor | 606/224 |
| 5,472,155 A * | 12/1995 | Mastrolia | 244/151 A |
| 5,534,011 A | 7/1996 | Greene et al. | 606/232 |
| 5,540,703 A * | 7/1996 | Barker et al. | 606/139 |
| 5,628,756 A * | 5/1997 | Barker et al. | 606/139 |
| 5,667,528 A | 9/1997 | Colligan | 606/224 |
| 5,683,417 A | 11/1997 | Cooper | 606/224 |
| 5,699,657 A * | 12/1997 | Paulson | 57/22 |
| 5,814,056 A | 9/1998 | Prosst et al. | 606/151 |
| 6,045,571 A | 4/2000 | Hill et al. | 606/228 |
| 6,083,243 A | 7/2000 | Pokropinski et al. | 606/230 |
| 6,139,565 A | 10/2000 | Stone et al. | 606/232 |
| 6,162,537 A | 12/2000 | Martin et al. | 428/373 |
| 6,241,747 B1 * | 6/2001 | Ruff | 606/216 |
| 6,296,659 B1 | 10/2001 | Foerster | 606/224 |
| 6,716,234 B2 | 4/2004 | Grafton | 606/228 |
| 6,991,636 B2 * | 1/2006 | Rose | 606/148 |
| 7,029,490 B2 | 4/2006 | Grafton et al. | 606/228 |
| 7,048,754 B2 * | 5/2006 | Martin et al. | 606/232 |
| 7,285,124 B2 | 10/2007 | Foerster | 606/139 |
| 7,329,272 B2 | 2/2008 | Burkhart et al. | 606/232 |
| 7,585,311 B2 * | 9/2009 | Green et al. | 606/232 |
| 7,658,751 B2 * | 2/2010 | Stone et al. | 606/232 |
| 7,799,073 B2 * | 9/2010 | Khalapyan | 623/2.37 |
| 7,803,173 B2 * | 9/2010 | Burkhart et al. | 606/232 |
| 7,905,903 B2 * | 3/2011 | Stone et al. | 606/232 |
| 7,981,139 B2 * | 7/2011 | Martin et al. | 606/232 |
| 7,981,140 B2 * | 7/2011 | Burkhart | 606/232 |
| 8,012,174 B2 | 9/2011 | Elattrache et al. | 606/232 |
| 8,100,942 B1 * | 1/2012 | Green et al. | 606/232 |
| 8,128,658 B2 * | 3/2012 | Kaiser et al. | 606/232 |
| 8,273,106 B2 * | 9/2012 | Stone et al. | 606/232 |
| 8,465,522 B2 * | 6/2013 | Burkhart | 606/232 |
| 8,690,915 B2 | 4/2014 | Hootstein | 606/232 |
| 8,808,326 B2 | 8/2014 | Gagliano | 606/228 |
| 2002/0029066 A1 * | 3/2002 | Foerster | 606/228 |
| 2003/0149448 A1 | 8/2003 | Foerster et al. | 606/232 |
| 2004/0097975 A1 * | 5/2004 | Rose | 606/145 |
| 2004/0133239 A1 | 7/2004 | Singhatat | 606/232 |
| 2005/0203620 A1 * | 9/2005 | Steiner et al. | 623/13.14 |
| 2005/0228448 A1 * | 10/2005 | Li | 606/232 |
| 2005/0267479 A1 * | 12/2005 | Morgan et al. | 606/73 |
| 2006/0079904 A1 | 4/2006 | Thal | 606/72 |
| 2006/0155328 A1 | 7/2006 | Foerster | 606/228 |
| 2006/0184203 A1 * | 8/2006 | Martin et al. | 606/232 |
| 2006/0259076 A1 * | 11/2006 | Burkhart et al. | 606/228 |
| 2006/0282081 A1 | 12/2006 | Fanton et al. | 606/72 |
| 2007/0010857 A1 * | 1/2007 | Sugimoto et al. | 606/232 |
| 2007/0135843 A1 * | 6/2007 | Burkhart | 606/232 |
| 2007/0191849 A1 * | 8/2007 | ElAttrache et al. | 606/72 |
| 2007/0288023 A1 | 12/2007 | Pellegrino et al. | 606/72 |
| 2008/0027446 A1 * | 1/2008 | Stone et al. | 606/73 |
| 2008/0065114 A1 * | 3/2008 | Stone et al. | 606/139 |
| 2008/0071299 A1 * | 3/2008 | Allinniemi et al. | 606/151 |
| 2008/0082127 A1 * | 4/2008 | Stone et al. | 606/232 |
| 2008/0082128 A1 * | 4/2008 | Stone | 606/232 |
| 2008/0255613 A1 | 10/2008 | Kaiser et al. | 606/232 |
| 2008/0262544 A1 | 10/2008 | Burkhart | 606/232 |
| 2009/0062854 A1 * | 3/2009 | Kaiser et al. | 606/232 |
| 2009/0082805 A1 * | 3/2009 | Kaiser et al. | 606/228 |
| 2009/0306711 A1 * | 12/2009 | Stone et al. | 606/232 |
| 2009/0318960 A1 | 12/2009 | Burkhart | 606/232 |
| 2012/0130422 A1 | 5/2012 | Hootstein | 606/228 |
| 2012/0158051 A1 | 6/2012 | Foerster | 606/232 |
| 2012/0172930 A1 | 7/2012 | Gagliano | 606/228 |
| 2012/0290003 A1 | 11/2012 | Dreyfuss | 606/232 |
| 2014/0163612 A1 | 6/2014 | Hootstein | 606/228 |

FOREIGN PATENT DOCUMENTS

| | | | |
|---|---|---|---|
| WO | 96/17544 | 6/1996 | A61B 17/04 |
| WO | 2004/082724 | 9/2004 | A61B 17/04 |

OTHER PUBLICATIONS

PCT International Search Report for PCT/US04/08313 1pg, Mailed Jan. 27, 2005.

PCT International Preliminary Report on Patentability for PCT/US04/08313 3pgs, Jan. 23, 2006.

PCT International Search Report for PCT/US04/08074 1pg, Mailed Dec. 7, 2004.

PCT Written Opinion of the ISA for PCT/US04/08074 5pgs, Mailed Dec. 7, 2004.

PCT International Preliminary Report on Patentability for PCT/US04/08074 4pgs, Jan. 25, 2005.

* cited by examiner

KNOTLESS SUTURE SYSTEM

CROSS-REFERENCE TO RELATED APPLICATIONS

This application claims priority to U.S. Provisional Application No. 61/417,081 filed Nov. 24, 2010, the entirety of which is incorporated herein by reference in its entirety.

BACKGROUND

Rotator cuff surgery continues to evolve. Initially surgery was performed using transosseous techniques. The advent of anchors enabled the procedures to be performed arthroscopically. Prior art approaches typically use either single or double row repair techniques with knotted sutures. The sutures act to hold the tendon next to the bone during the healing process.

The evolution has gone from single row to double row repairs. However, these constructs require surgeons to know how to tie complicated knots which are technically challenging. The suture knots in the tissue can be bulky and create a painful impingement of the tendon on the bone. This is because the knots end up on top of the cuff, in the subacromial space, and have the opportunity to rub on the acromion as the arm is raised. Because non-absorbable suture materials are used for these types of repairs, the suture and associated knots are not absorbed into the body, and hence provide a constant, painful reminder of their presence. Furthermore, there are issues surrounding the use of tying knots which include knot security and loop security. There is also the potential for these knots to increase the chance of tissue reaction. Another concern is the potential for knots to create a "clicking" sound associated with patient irritation.

Better instruments and improved anchor designs facilitated knotless single row configurations. Next, double row transosseous equivalent repairs were developed. Many of these techniques still require complicated knots. Again, the problems previously described with knots are still issues of this technique. One potential advantage of this technique is that there is independent medial row fixation. Another derivative of this repair construct is a knotless "bridge" technique. While this technique eliminates the need to tie knots, the medial and lateral row fixation is dependent on one another. In other words, if the lateral row fails then so does the corresponding medial row. An arthroscopic technique that enables a truly knotless double row transosseous repair with application of medial pressure is desirable. An improved suture system and methods of using such a suture system would address the concerns previously described and would also allow for surgeons of various skill levels to perform the technique arthroscopically and without the need for knot tying.

DETAILED DESCRIPTION

The present invention provides an improved knotless suture apparatus for suturing of soft tissue at a surgical repair site. In an exemplary embodiment described herein, the apparatus is used to secure soft tissue to a bone structure, specifically the humeral bone of the human shoulder. The length of suture is desirably looped through soft tissue, such as a rotator cuff tendon, to approximate and fix the soft tissue with respect to the body cavity (e.g., bone structure). It should be understood, however, that the suture anchor apparatus may be utilized to secure a length of suture to body cavities other than in a bone structure, and may even be used to anchor the suture outside of a body cavity, merely to a predetermined location within the body. In this regard, the preferred apparatus includes an interwoven suture configuration that may be variably arranged and adjusted freely and then anchored or secured without knots.

Figure 1:
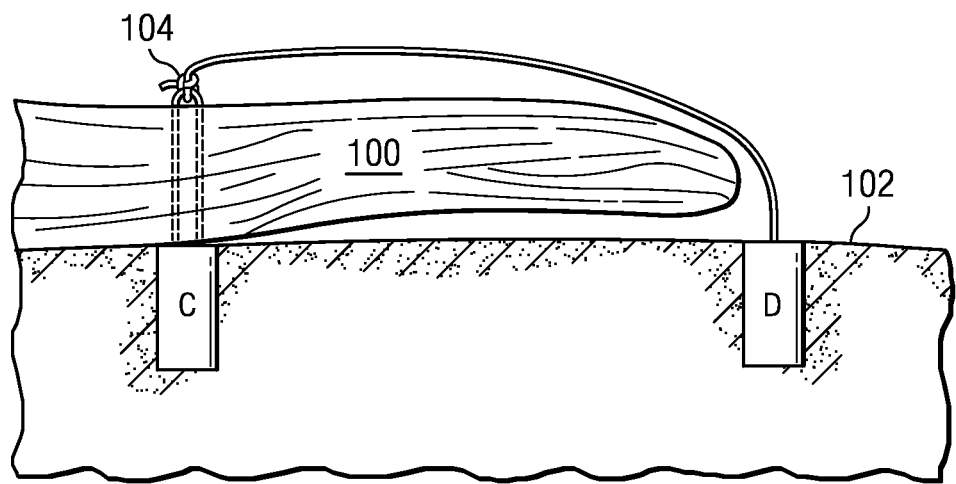
FIG. 1 illustrates a side view of a traditional knotted double row repair.
Figure 2:
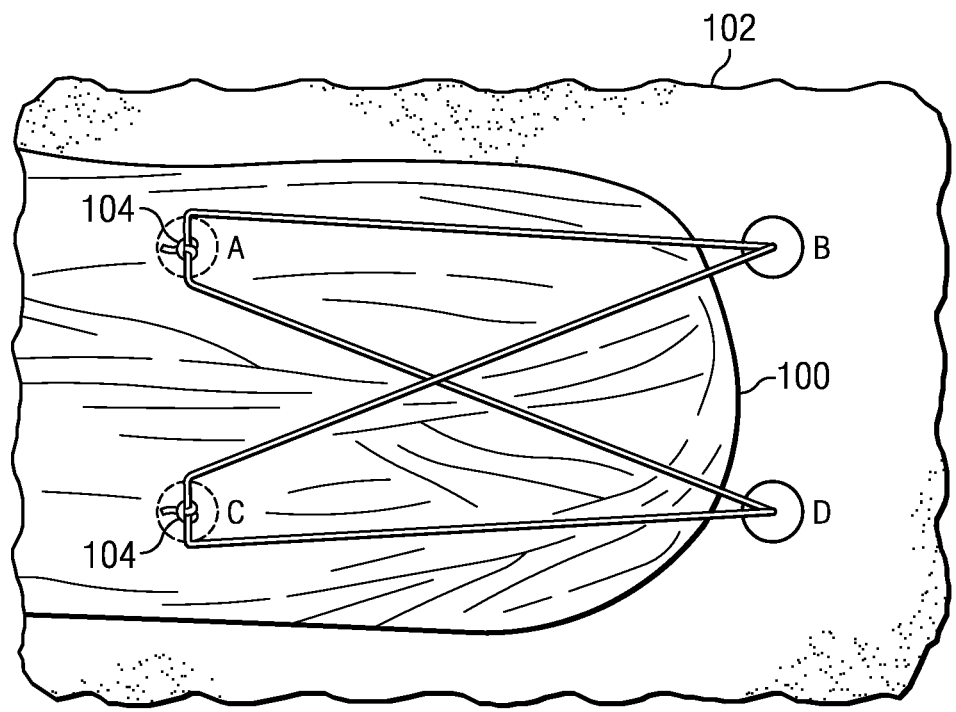
FIG. 2 illustrates a top view of a traditional knotted double row repair.

A traditional knotted double row, transosseous equivalent repair is shown in FIGS. 1 (side view) and 2 (top view). Anchors A and C (medial) and B and D (lateral) are disposed beneath the torn tendon 100 and implanted into the supporting bone 102. Sutures are attached to these anchors, passed upward through the tendon. Knots 104 are tied in each suture above the corresponding medial anchor. These knots supply medial compression. The sutures are then drawn to lateral implants B to supply additional compression over the length of the tissue. Advantageously, the knots supply a degree of medial compression even if the connection to the lateral implant fails. Unfortunately, this benefit is realized using knots and therefore produces all of the drawbacks associated with knots.

Figure 3:
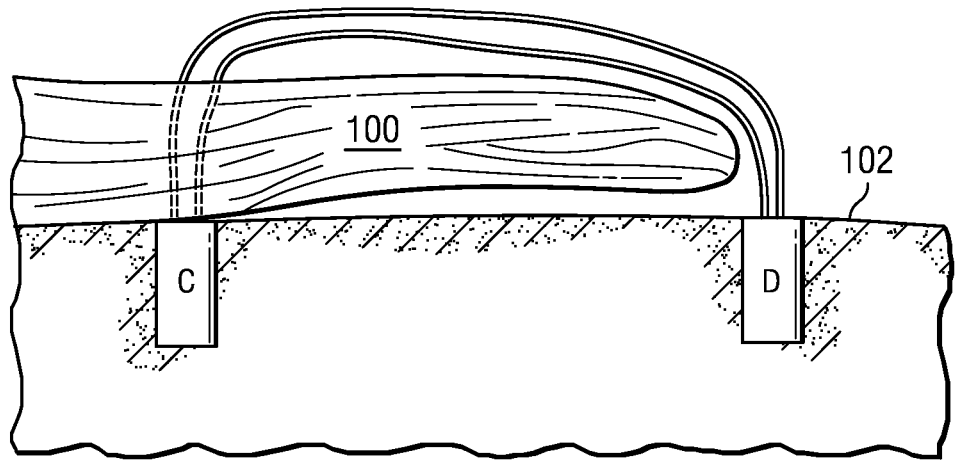
FIG. 3 illustrates a side view of a present version knotless double row repair.
Figure 4:
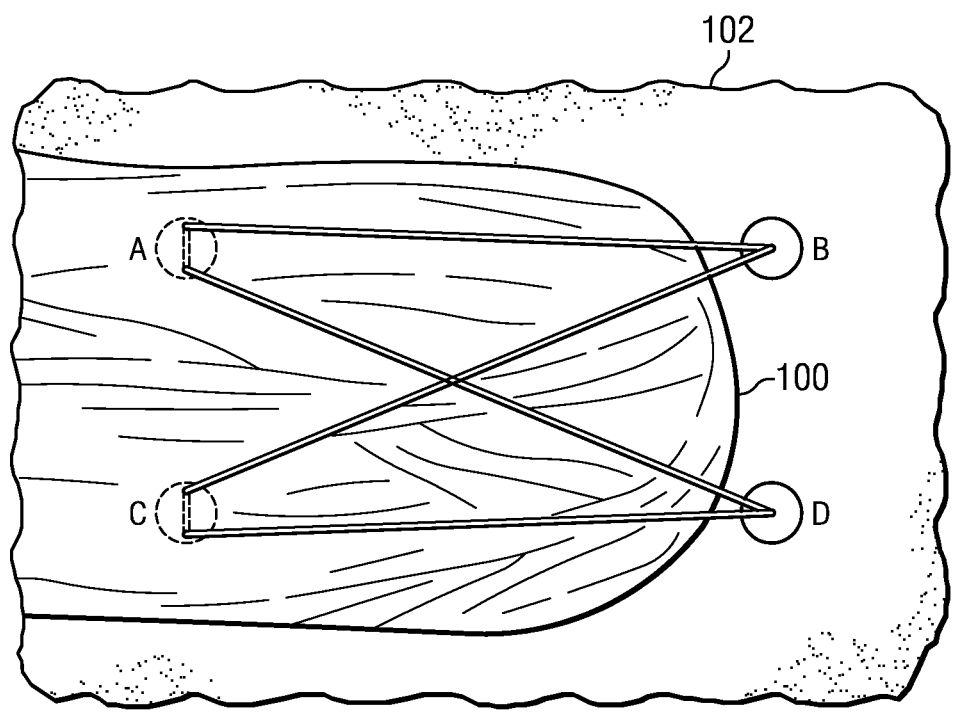
FIG. 4 illustrates a side view of a present version knotless double row repair.

A current version of a knotless double row, transosseous equivalent repair is shown in FIGS. 3 (side view) and 4 (top view). The suture is then drawn across the tissue and attached to anchors. Advantageously, this technique omits knots. Unfortunately, due to the absence of knots, this configuration only provides pressure at the medial implants if the lateral connection remains intact. If the connection to the lateral implant fails, the entire repair fails.

Figure 5A:
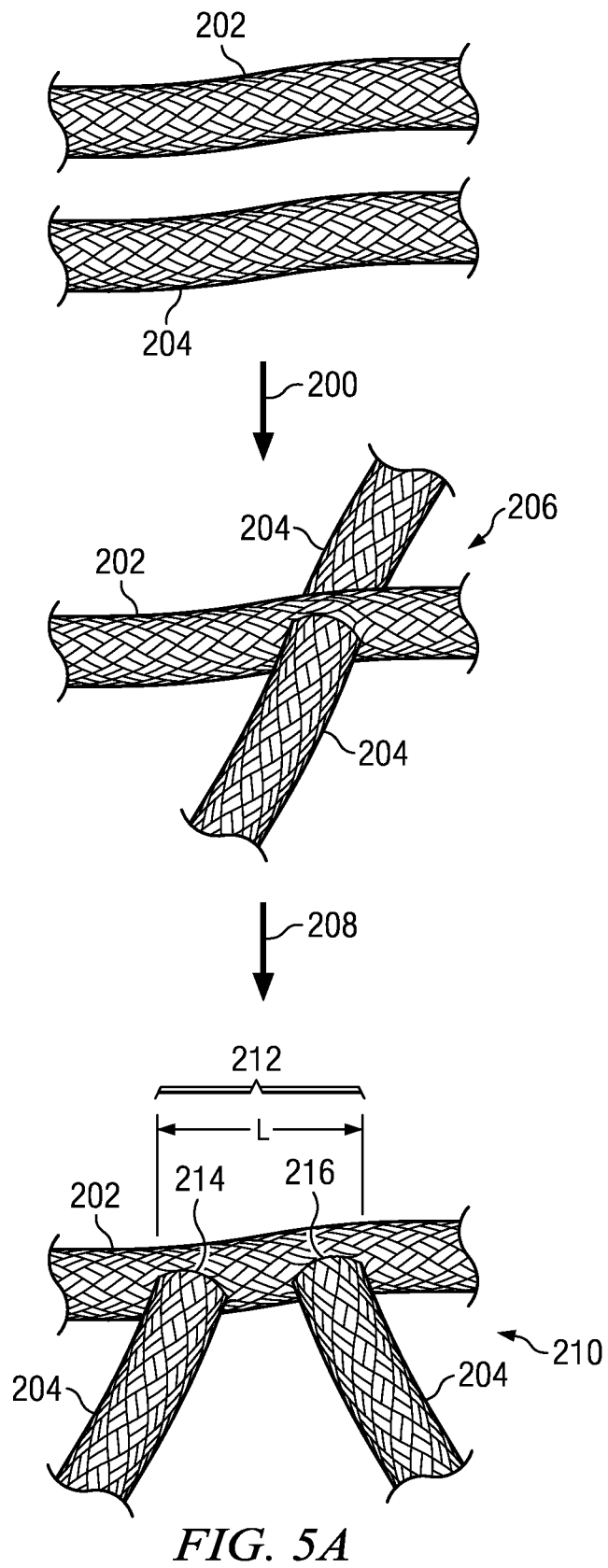
FIG. 5A illustrates a view of an interwoven suture configuration in accordance with at least some embodiments.

The present disclosure pertains to a novel suture that permits single and double row repair to be performed without using knots. The presently described suture configuration enables the true knotless double row transosseous technique to be performed arthroscopically by providing a joined, double armed suture system with two independent suture strands or limbs on both the medial and lateral sides that may be secured in knotless fashion. Such a suture system further facilitates soft tissue repair by establishing an adjustable suture bridge for optimal tissue-bone footprint reestablishment in the area adjacent the joined suture junction. In certain embodiments, two lengths of suture are interwoven over a predetermined length, such that the predetermined length of combined sutures forms a joined suture connection portion of the interwoven suture combination referred to by the applicant herein as a "belt." FIG. 5A illustrates a first suture 202 and a second suture 204. In step 200, suture 204 is passed through suture 202. In one embodiment, suture 202 is a braided suture to facilitate this interweaving step, such that at one discrete location the braids of suture 202 are slightly separated to allow suture 204 to be interwoven through the separated braids of suture 202. Step 200 produces suture 206 which is characterized by a single instance of interweaving suture 204 into suture 202. In step 208, suture 204 is again passed through suture 202 at a second location where, for example, the braids of suture 202 are slightly separated, to produce suture system 210. This second location of interweaving suture 204 through suture 202 establishes "belt" 212 which has a length L. The precise dimension or magnitude of L can be controlled by either repeating step 208 multiple times (i.e., by repeating the interweaving step to create multiple locations or points of insertion and interweaving of suture 204 into suture 202) or by simply increasing the distance between the two points of insertion 214 and 216.

Figure 5B:
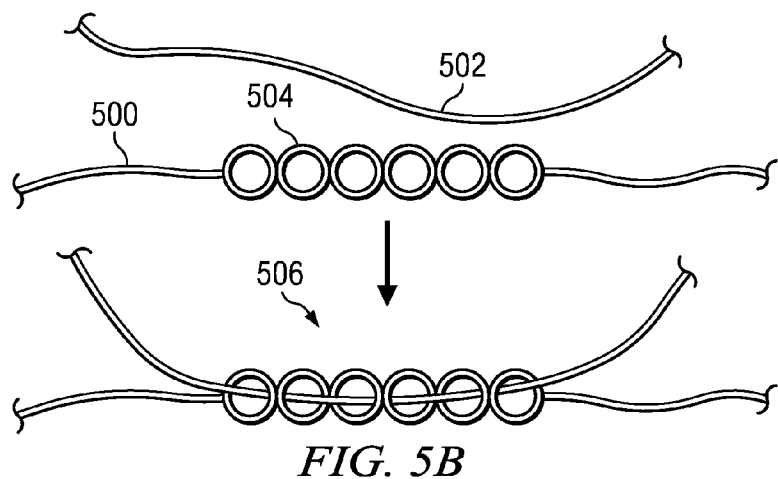
FIG. 5B illustrates a view of an interwoven suture configuration in accordance with at least some embodiments.

It is contemplated that one distinct length of suture need not completely penetrate the other to be interwoven. The first suture can be partially inserted into the core of the second suture and reemerge on the same side before the first suture is completely penetrated. In this manner, the suture combination may be described as a "chromosome" type connection, where each length of suture touches the other and is connected or attached at a common point, either by interweaving one of the lengths of suture into a portion of the other or by some similar manner of joined connection between each respective length of suture without the need for knot tying. Additionally, a joined suture system is contemplated where one of the lengths of suture has a smaller diameter than the second length of suture, such that the smaller diameter suture may slide inside a hollow portion of the second, larger diameter suture to thereby facilitate an interwoven connection between the two. The first suture can also be otherwise stitched to the second suture. Alternatively or additionally, two sutures can be connected by passing each adjacently through a hollow band. Similarly to the belt configuration, the hollow band may be a desired length, dimension, or magnitude. Another method for forming the belt is to use a suture such as suture 500 of FIG. 5B in conjunction with suture 502. Suture 500 includes one or more rings 504. To form a combined suture system according to these embodiments, suture 502 is passed through rings 504 of suture 500. The width of the rings defines the width of the belt. Generally, the belt may be from about 1 mm to about 15 mm in length. In another embodiment, the belt may be from about 5 mm to about 12 mm in length.

Figure 6:
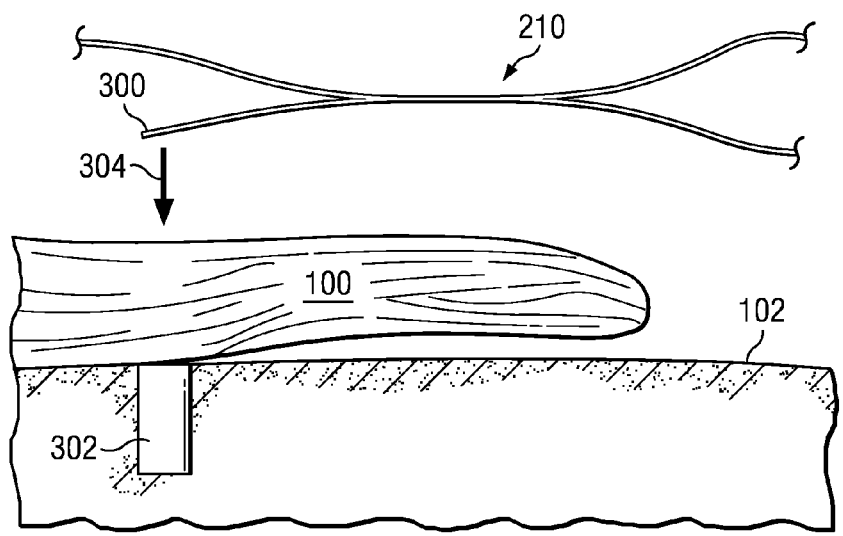
FIG. 6 illustrates a side view of an interwoven suture configuration adjacent to soft tissue in accordance with at least some embodiments.
Figure 7:
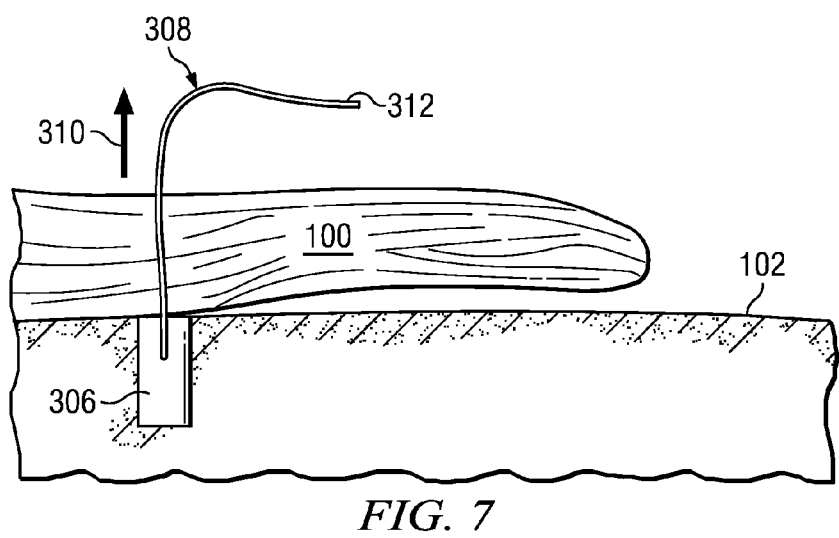
FIG. 7 illustrates a side view of a terminus of a suture configuration passed retrograde through soft tissue in accordance with at least some embodiments.
Figure 7A:
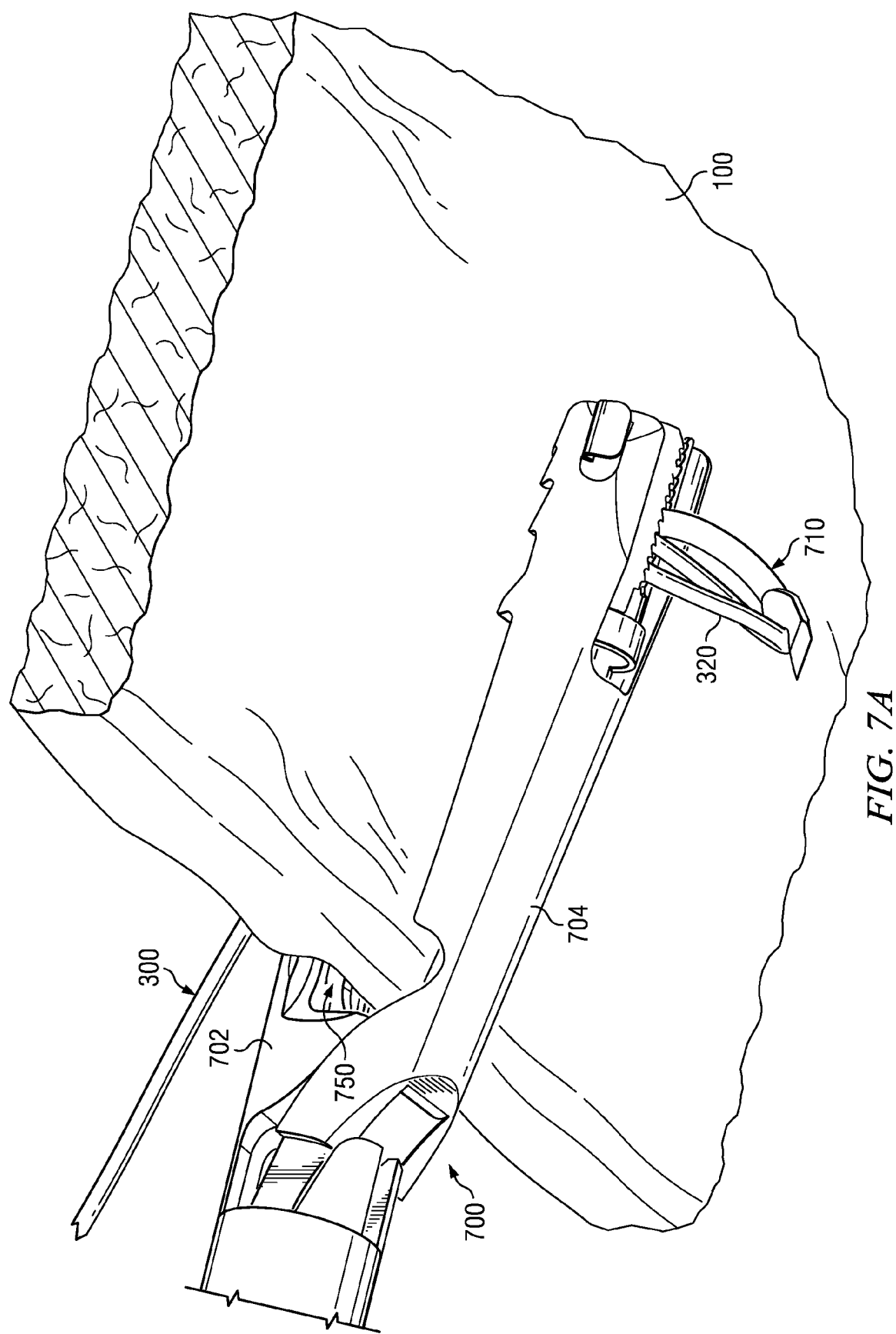
FIG. 7A illustrates a suturing device for use in deploying the suture configuration described herein in accordance with at least some embodiments.

Referring to FIG. 6, the terminus 300 of suture system 210 is passed through the soft tissue 100 downward, or retrograde, from top of the tissue to bottom in the direction of arrow 304, and then attached to anchor 302. In one embodiment, anchor 302 is a knotless suture anchor. This is a stark contrast with present surgical techniques which utilize an anchor that includes suture 308 which is passed upwards, or anterograde, from bottom of the tissue to top in the direction of arrow 310, as illustrated in FIG. 7. In this technique, terminus 312 is later tied to the corresponding end of the same suture. In order to facilitate retrograde passing of the joined suture system presently described herein, the modified use of a suture passing device such as the FirstPass® device (described in U.S. Patent Application Publication No. 2011/0118760 and incorporated by reference herein) in conjunction with the combined suture system described herein is contemplated. Referring now to FIG. 7A, a suturing device 700 is inserted through a trocar cannula until jaws 702, 704 reach the tissue to be treated. In order to facilitate retrograde passing of the combined suture system, suturing device 700 is inserted with the handle oriented up so that upper jaw 704 is beneath the tissue and lower jaw 702 is above the tissue. Soft tissue 100 is introduced into the space between the upper jaw 704 and the lower jaw 702, and device 700 is actuated so that upper jaw 704 may clamp or grasp the soft tissue 100 and immobilize it between the upper jaw 704 and the lower jaw 702.

With the position of the soft tissue 100 grasped between jaws 702, 704 and within the tissue receiving area 750 device 700 deemed satisfactory, needle 710 may be deployed to not only penetrate the top side of the soft tissue, but to also capture and pass the combined suture system through the soft tissue. In order to configure the combined suture system for retrograde passing through the soft tissue using device 700, at least one of the suture terminus 300 (see FIG. 6) or suture limbs (i.e., see FIG. 8A and suture system 210 with suture limbs 202A-B or 204C-D) of a combined suture system is positioned within the suture retaining area of device 700. In other contemplated embodiments, more than one suture terminus or suture limb of a combined suture system may be engaged by a needle 710 of device 700 and subsequently passed in a retrograde fashion through soft tissue 100. In the fully extended position of needle 710, the selected length of suture 300 that has been drawn through soft tissue 100 forms a suture portion 320 which protrudes from the soft tissue and is disposed below upper jaw 704. In certain embodiments, suture portion 320 may form a looped configuration for later manipulation to a bone anchor.

Figure 8A:
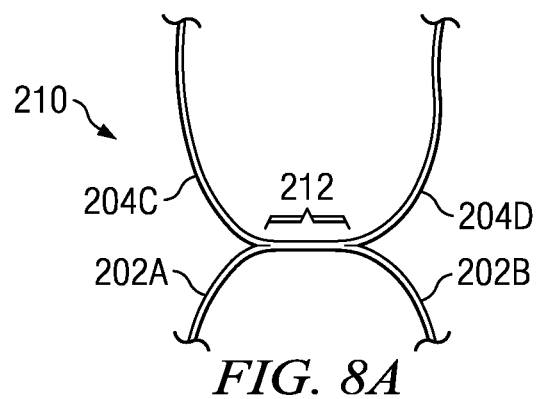
FIG. 8A illustrates a view of an interwoven suture configuration in accordance with at least some embodiments.
Figure 8B:
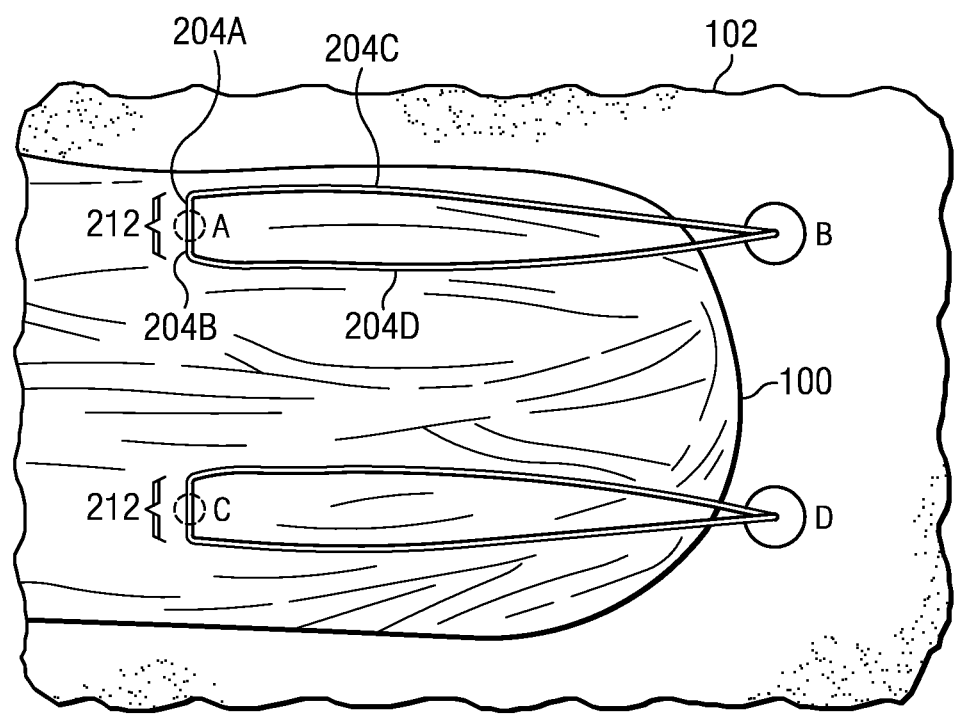
FIG. 8B illustrates a top view of a deployed interwoven suture configuration in accordance with at least some embodiments.

FIG. 8A depicts a combined suture system 210 according to certain embodiments with an "X" or "chromosome" configuration. Suture system 210 has a first suture 202 and a second suture 204 with four separate suture limbs (202A-B and 204C-D) and is further characterized by belt 212 where the individual lengths of suture are joined. Depending on the precise interweaving pattern, a given length of suture can provide any two of these limbs. Referring to FIGS. 8A and 8B, one repair technique using suture system 210 involves passing limb 202A down through soft tissue 100. Limb 202B is similarly passed down through the tissue at some small distance from limb 202A. These limbs 202A, 202B are then each inserted into a medially placed knotless anchor/implant A, such as the Opus® Magnum® 2 implant, Magnum X implant, or SpeedScrew® implant. As tension is applied to suture system 210 and the limbs 202A and 202B are drawn into the implant A, the belt 212 of the suture begins to compress the tissue medially whereas belt 212 defines the length of the mattress portion of the stitch on the superior (bursal side) aspect of the tissue. As described above, the length L of belt 212 is selectable to accommodate the repair construct desired by the practitioner, wherein for example a greater length L may be desirable to increase the compression footprint applied by belt 212 to the adjacent soft tissue. A similar procedure is repeated for implant C, where the belt 212 on a second suture system 210 compresses the tissue at the insertion point of the suture limbs into the anchor. After two suture systems 210 have been set into medial implants A and C, respectively, limbs 204C and 204D of each suture are spanned out and inserted into laterally placed knotless implants B and D (see FIG. 8B) and then appropriated tensioned and secured. It should be noted that the span of limbs 204C and 204D laterally across the soft tissue 100 also serves to compress the tissue to the underlying bone structure in an effort to restore the anatomical footprint of the damaged tissue with respect to the bone.

Figure 8C:
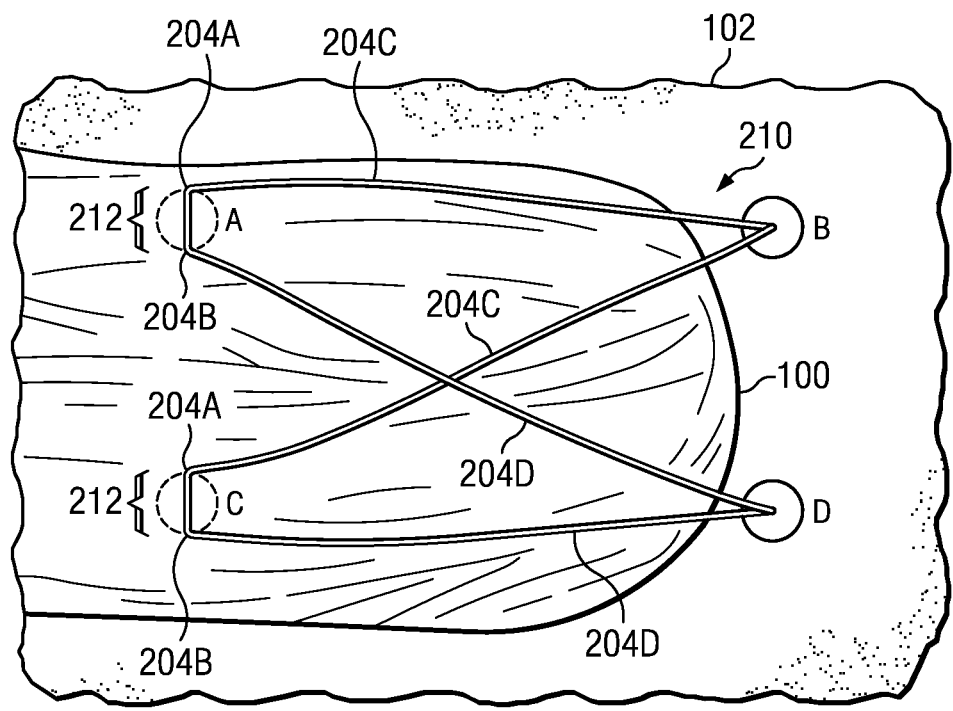
FIG. 8C illustrates a top view of a deployed interwoven suture configuration in accordance with at least some embodiments.

Referring now to FIG. 8C, in certain other embodiments, a practitioner may, after securing medial limbs 204A, 204B into a lateral implant A and forming a belt 212, span one lateral limb 204C of a suture system 210 from a medial implant into one lateral implant, both implants disposed generally anteriorly with regard to the patient's anatomical midline (e.g. A to B) followed by spanning a second lateral limb 204D from the same medial implant to a different lateral implant, the second lateral implant disposed more posteriorly in comparison to the first lateral implant (e.g. A to D). Similarly, a second suture system 210 may be used in conjunction after securing the two medial limbs to the medial implant and forming a belt 212 to span one lateral limb from a second medial implant into the second lateral implant (e.g. C to D) followed by spanning a second lateral limb from the same medial implant to the first lateral implant (e.g. C to B). In particular, this configuration has criss-crossing suture limbs over the top of the rotator cuff potentially increasing anatomical footprint compression of the soft tissue to the underlying bone structure. The repair provides medial row compression and fixation without the need for knots. Furthermore, medial row fixation is independent of the lateral row as a function of tissue securement in the vicinity of belt 212. In the event of a partial failure, the width of belt 212 provides a downward force that helps hold the tissue against the bone at least in the area of the medial implant.

Figure 8D:
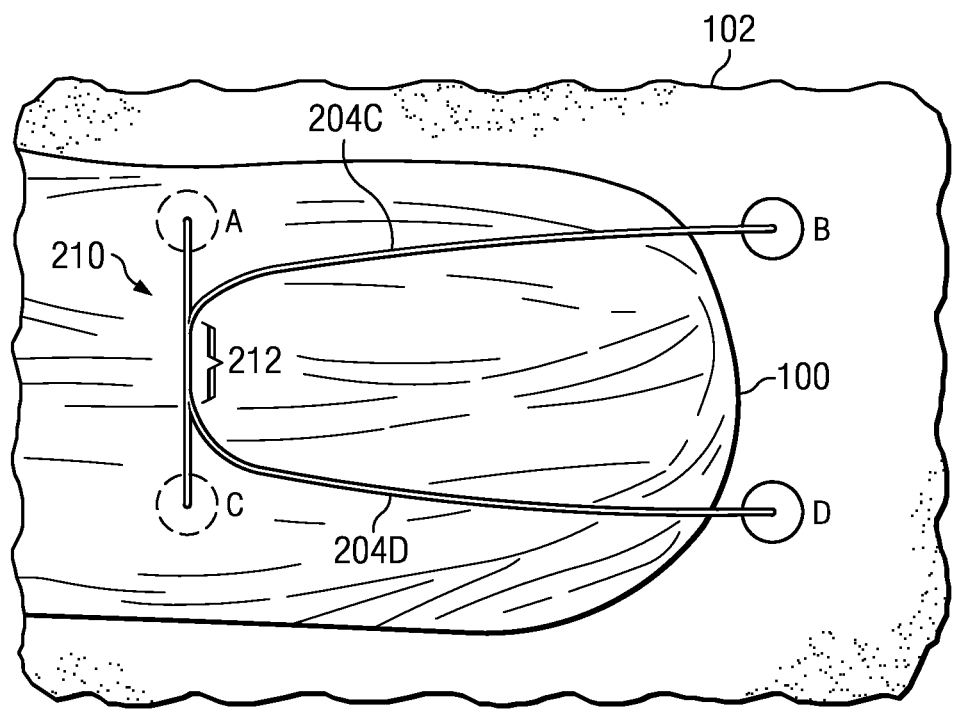
FIG. 8D illustrates a top view of a deployed interwoven suture configuration in accordance with at least some embodiments.

FIG. 8D depicts another configuration where the two medial limbs (202A and 202B) are each attached to two different medial implants (A and C). The belt 212 is disposed between these two implants. The remaining lateral limbs (204C and 204D) are attached to two lateral implants B and D. In this configuration, belt 212 spans between the two medial implants thereby providing medial row compression and fixation across a broader footprint. Additionally, this configuration ideally requires only one suture system 210, thereby allowing the practitioner to limit the exercise of suture passing to two instances.

In another contemplated embodiment, not shown, more than two strands are interwoven into a single belt position. For example, three sutures may be interwoven at a single belt thereby producing a suture with six limbs (e.g., three medial suture limbs and three lateral suture limbs) and one belt.

Figure 9:
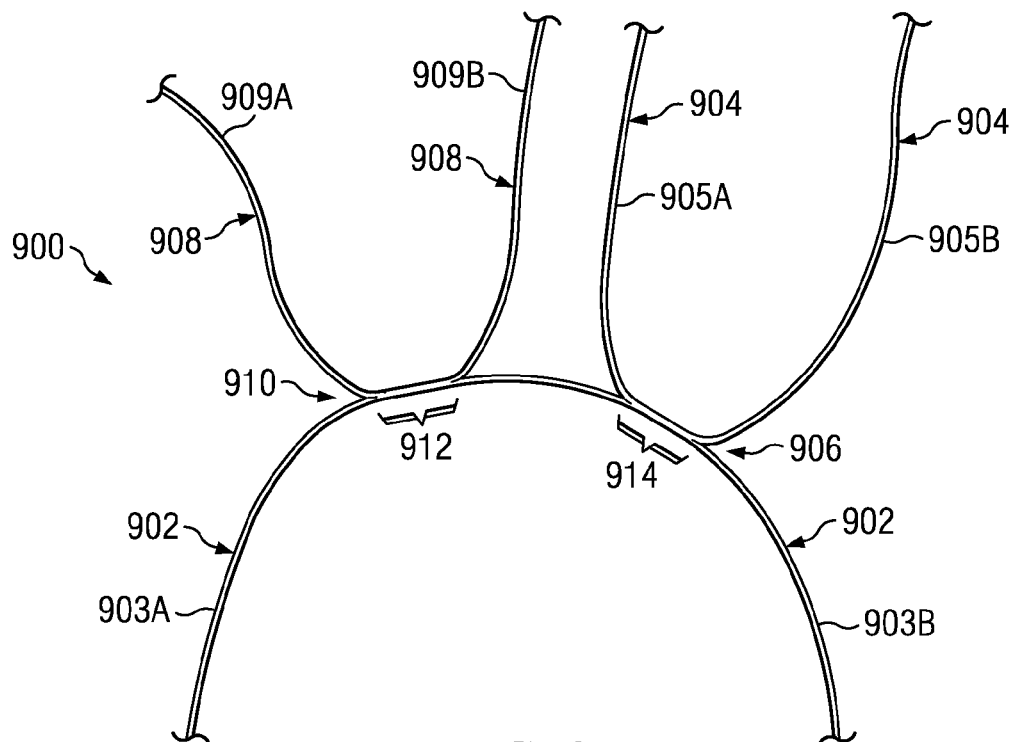
FIG. 9 illustrates a top view of a interwoven suture "W" configuration in accordance with at least some embodiments.

Referring now to FIG. 9, a suture system 900 with a "W" configuration is illustrated. Suture system 900 is similar to suture system 210 except in that one of the sutures 902 has a third suture 904 woven into it at point 906, thereby establishing a second belt 914. First suture 902 is connected to second suture 908 at point 910 to establish belt 912. First suture 902 is also connected to third suture at point 906 to establish belt 914. The second suture 908 and third suture 904 are not directly connected to one another. The W is formed by the two limbs (905A, 905B) of suture 904 and the two limbs (909A, 909B) of suture 908. The second belt is useful for spanning the gap between adjacent medial implants (e.g. implants A and C of FIG. 8D). Additionally, the limbs 903A, 903B of suture 902 are each secured to medial row implants (i.e., implants A and C) where the lateral row limbs are secured to lateral row implants (e.g., limbs 909A, 909B to implant B, limbs 905A, 905B to implant D).

Various materials may be used to form the suture system according to the embodiments described herein. For example, a number two high-strength polyethylene absorbable suture may be used. Other suitable suture materials, both absorbable and non-absorbable, are known in the art and are contemplated for use with the present invention. Polyester, polyglycolic acid, polyurethane and other synthetic polymer sutures are well known. The suture could be traditional-type high strength sutures or flat-based tape type sutures.

Various methods for forming the present sutures are contemplated. For example, the suture may be interwoven by the surgeon during surgery by interweaving the two sutures during the operation. Alternatively, the suture may be similarly interwoven prior to the operation. The suture may also be manufactured in an X configuration. For example, a braided suture may be partially unwoven at its ends to produce the X configuration.

Figure 10:
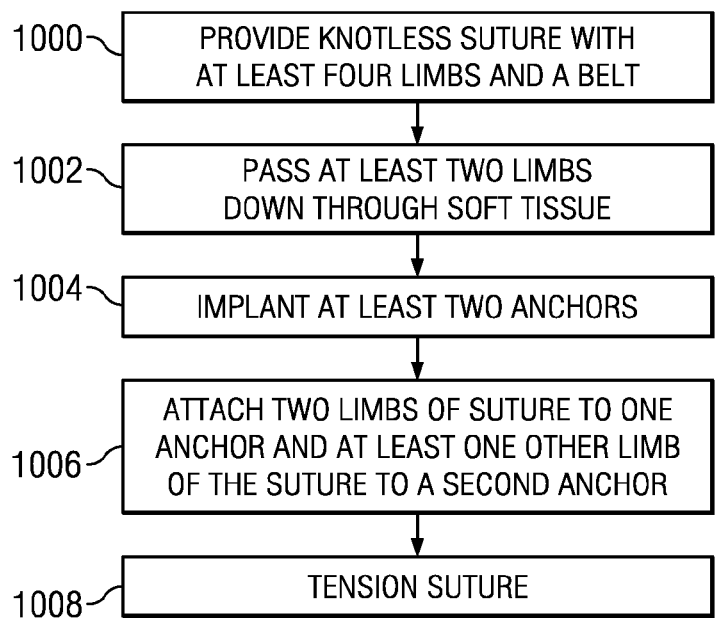
FIG. 10 illustrates a flow diagram of a procedure to secure connective tissue to bone according to at least certain embodiments in the present disclosure.

In another embodiment, the invention pertains to a method of performing soft tissue reattachment to bone. Referring to FIG. 10, the method begins with step 1000 in which a knotless interwoven suture, such as suture system 210, is provided that has at least four limbs and at least one belt. In step 1002 at least two of these limbs are passed downward, through soft tissue. A suture shuttle may be used to pass the interwoven suture through the soft tissue. In step 1004 at least two knotless anchors (one medial, one lateral) are implanted into bone. In one embodiment, at least four anchors are implanted and the repair is performed in the manner of a double row repair technique. The implants are disposed under or adjacent tom soft tissue. In step 1006 two limbs of suture are attached to one anchor and at least one limb of the suture to a second anchor. In step 1008 the limbs of the suture are tensioned across the top surface of the soft tissue to cause its bottom surface to rest securely against the bone. The suture limbs are tightened such that the belt is disposed above a corresponding anchor. The tensioning of step 1008 is dialed by means of the knotless lateral anchors.

While preferred embodiments of this invention have been shown and described, modifications thereof can be made by one skilled in the art without departing from the scope or teaching herein. The embodiments described herein are exemplary only and are not limiting. Because many varying and different embodiments may be made within the scope of the present teachings, including equivalent structures or materials hereafter thought of, and because many modifications may be made in the embodiments herein detailed in accordance with the descriptive requirements of the law, it is to be understood that the details herein are to be interpreted as illustrative and not in a limiting sense.

The invention claimed is:

1. A suture system for use arthroscopically consisting of:
a first and second suture, each of the first and second suture having two suture limbs such that the first and second suture form four suture limbs; wherein at least one of the four limbs terminates in a needleless terminus, wherein the at least one needleless terminus is operable to be engaged by a needle of a suture passing instrument so as to pass the at least one needleless terminus and associated suture limb through soft tissue;
wherein a portion of the first and second sutures are at least partially joined together to form a single suture junction, the single suture junction having a length and wherein the single suture junction is formed by partially inserting the first suture through a wall of the second suture into and along a core of the second suture, and then re-emerging through a wall of the second suture; and wherein the first suture is completely contained within the second suture for the length of the single suture junction; and wherein the four suture limbs extend away from each other defining the single suture junction length, and wherein two of the suture limbs are configured to extend from the single suture junction and be coupled to a first fixation device, located within bone and under the soft tissue and the other two suture limbs are configured to extend from the single suture junction and be coupled to a second fixation device located within bone and adjacent to, but not under, the soft tissue, each of the four limbs configured to span the soft tissue from the suture junction to one of the fixation devices and compress the soft tissue to bone; and wherein the entire length of the single suture junction is configured to abut the soft tissue so as to define a compression footprint on the soft tissue and compress the soft tissue against the bone, directly under the footprint.

2. The suture system of claim 1, wherein the first suture and the second suture are each formed of a plurality of braided fibers.

3. A suture system for use arthroscopically consisting of:
a first and second suture, the first and second sutures each having two suture limbs such that the first and second sutures form four suture limbs;
a suture passing device having a needle configured to engage at least one suture limb with a needleless terminus and pass the limb and terminus through soft tissue;
wherein a portion of the first and second sutures are at least partially joined together to form a single suture junction, the single suture junction having a length and wherein the single suture junction is formed by partially inserting the first suture into and along an internal core of the second suture and then re-emerging and wherein the second suture has a continuous lumen except for gaps, the gaps being formed by the first suture only, as the first suture is inserted and re-emerged; and
wherein the four suture limbs extend away from each other defining the single suture junction length, and wherein two of the suture limbs are configured to be coupled to a first fixation device located within bone and under the soft tissue and the other two suture limbs are configured to be coupled to a second fixation device located within bone and adjacent to, but not under, the soft tissue, each of the four limbs configured to span the tissue from the suture junction to either the first fixation device or the second fixation device and compress the tissue to bone; and wherein the entire length of the single suture junction is configured to abut a target tissue so as to define a compression footprint on the target tissue and compress the target tissue against the bone, directly under the footprint.

4. The suture system of claim 3, wherein the gaps are formed by slightly separating the plurality of braided fibers of the second suture.

5. A suture system for single or double row rotator cuff repair consisting of:
a first and second suture joined together at a single suture junction, wherein the first suture is completely contained within the second suture for an entire length of the single suture junction, and wherein each of the first and second sutures have two suture limbs such that the first and second sutures form four suture limbs; and
wherein each of the four suture limbs are configured to span a rotator cuff tendon either from the single suture junction to a first fixation device located within bone and under the tendon or from the single suture junction to a second fixation device located within bone and adjacent to, but not under, the tendon or from the suture junction to a third fixation device located adjacent the second fixation device and compress the tendon to bone.

6. A suture system for use arthroscopically consisting of:
a first and second suture, the first and second sutures each having two suture limbs such that the first and second sutures form four suture limbs;
wherein a portion of the first and second sutures are at least partially joined together to form a single suture belt, the single suture belt having a length and wherein the single suture belt is formed by partially inserting the first suture through a wall of the second suture into and along a core of the second suture, and then re-emerging through a wall of the second suture; and wherein the first suture is completely contained within the second suture for the length of the single suture belt; and wherein the four suture limbs extend away from each other defining the single suture belt length, and wherein two of the suture limbs are configured to extend from the single suture belt and be coupled to a first fixation device, located within bone and under a soft tissue and the other two suture limbs are configured to extend from the single suture belt and be coupled to a second fixation device located within bone and adjacent to, but not under, the soft tissue, each of the four limbs configured to span the soft tissue from the suture belt to one of the fixation devices and compress the soft tissue to bone; and
wherein an entire length of the single suture belt is configured to abut the soft tissue so as to define a compression footprint on the soft tissue and compress the soft tissue against the bone, directly under the footprint.

* * * * *